(12) United States Patent
Lavigne

(10) Patent No.: US 9,713,566 B2
(45) Date of Patent: Jul. 25, 2017

(54) HEATING AND COOLING MAT ASSEMBLY

(71) Applicant: Corey Lavigne, Marktham, IL (US)

(72) Inventor: Corey Lavigne, Marktham, IL (US)

( * ) Notice: Subject to any disclaimer, the term of this patent is extended or adjusted under 35 U.S.C. 154(b) by 260 days.

(21) Appl. No.: 14/560,200

(22) Filed: Dec. 4, 2014

(65) Prior Publication Data
US 2016/0158094 A1    Jun. 9, 2016

(51) Int. Cl.
*A47C 27/08* (2006.01)
*A61H 23/02* (2006.01)
*A61F 7/08* (2006.01)
*A61F 7/00* (2006.01)

(52) U.S. Cl.
CPC .............. *A61H 23/02* (2013.01); *A61F 7/007* (2013.01); *A61F 7/0097* (2013.01); *A61F 7/08* (2013.01); *A61F 2007/0054* (2013.01); *A61F 2007/0072* (2013.01); *A61F 2007/0078* (2013.01); *A61F 2007/0093* (2013.01); *A61F 2007/0094* (2013.01); *A61H 2201/0242* (2013.01)

(58) Field of Classification Search
CPC . A61H 23/02; A61H 2201/0242; A61F 7/007; A61F 7/08; A61F 2007/0078; A61F 2007/0054; A61F 2007/0072; A61F 2007/0093; A61F 2007/0094
See application file for complete search history.

(56) References Cited

U.S. PATENT DOCUMENTS

| 2,998,817 | A |   | 9/1961  | Armstrong |
|-----------|---|---|---------|-----------|
| 3,014,117 | A | * | 12/1961 | Madding ............... A47J 41/005 219/217 |
| 4,231,355 | A |   | 11/1980 | Hara |
| 5,016,618 | A |   | 5/1991  | Simmons |
| 5,020,517 | A | * | 6/1991  | Foster, Jr. .......... A61H 23/0263 297/284.1 |
| 5,174,285 | A | * | 12/1992 | Fontenot ................... A61F 7/00 165/46 |
| D471,636  | S |   | 3/2003  | Yu |
| 6,568,006 | B1 |  | 5/2003  | Hyland |
| 7,959,657 | B1 | * | 6/2011 | Harsy .................... A61F 7/007 607/104 |
| 8,613,762 | B2 | * | 12/2013 | Bledsoe .................. A61F 7/02 165/46 |
| 2006/0048520 | A1 | * | 3/2006 | Huang ................. F24F 5/0042 62/3.5 |
| 2007/0010766 | A1 |   | 1/2007  | Gill et al. |
| 2008/0092295 | A1 | * | 4/2008 | Flick .................. A61G 7/05776 5/600 |

(Continued)

*Primary Examiner* — Steven Douglas

(57) ABSTRACT

A heating and cooling mat assembly includes a mat having a bottom wall, a top wall and a perimeter wall. A conduit is positioned in the man and has fluid therein. A pump is in fluid communication with the conduit to pump the fluid through the conduit. A heat emitter is thermal communication with the liquid in the conduit. The heat emitter warms the liquid when the heat emitter is turned on. A cartridge is removably couplable to the mat. The cartridge includes a pair of first ports. The conduit is in fluid communication with a pair of second ports. Each of the first ports is removably coupled to one of the second ports to fluidly couple the conduit to the cartridge. The cartridge is fillable with a cold fluid so that the conduit is cooled when the pump is turned on and the cartridge is coupled to the conduit.

8 Claims, 5 Drawing Sheets

(56) References Cited

U.S. PATENT DOCUMENTS

2010/0106229 A1* 4/2010 Gammons ............. A61F 7/0085
607/104
2011/0289683 A1* 12/2011 Mikkelsen ........... A47C 21/048
5/421
2013/0041297 A1 2/2013 Garcia et al.

* cited by examiner

HEATING AND COOLING MAT ASSEMBLY

BACKGROUND OF THE DISCLOSURE

Field of the Disclosure

The disclosure relates to mat devices and more particularly pertains to a new mat device for relaxing a person utilizing warmth, cooling and massaging features.

SUMMARY OF THE DISCLOSURE

An embodiment of the disclosure meets the needs presented above by generally comprising a mat that has a bottom wall, a top wall and a perimeter wall that is attached to and extends between the bottom and top walls. A conduit is positioned in the mat and is placed in a serpentine pattern within the mat. The conduit has fluid therein and a pump is in fluid communication with the conduit. The pump pumps the fluid through the conduit when the pump is turned on. A heat emitter is thermal communication with the liquid in the conduit. The heat emitter warms the liquid when the heat emitter is turned on. A cartridge is removably couplable to the mat. The cartridge includes a pair of first ports. The conduit is in fluid communication with a pair of second ports. Each of the first ports is removably coupled to one of the second ports to fluidly couple the conduit to the cartridge. The cartridge is fillable with a cold fluid so that the conduit is cooled when the pump is turned on and the cartridge is coupled to the conduit.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
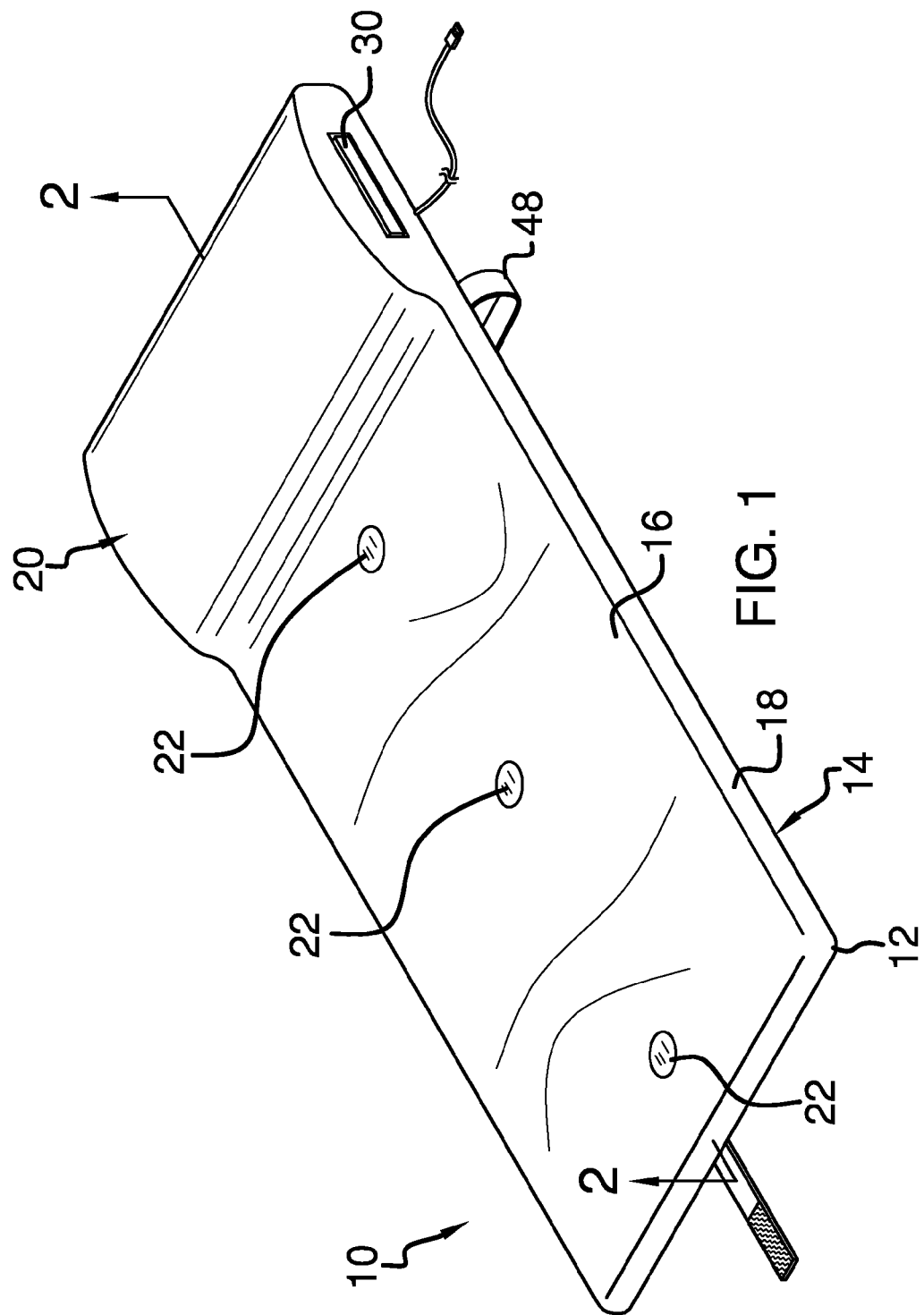
FIG. 1 is a perspective view of a heating and cooling mat assembly according to an embodiment of the disclosure.
Figure 2:
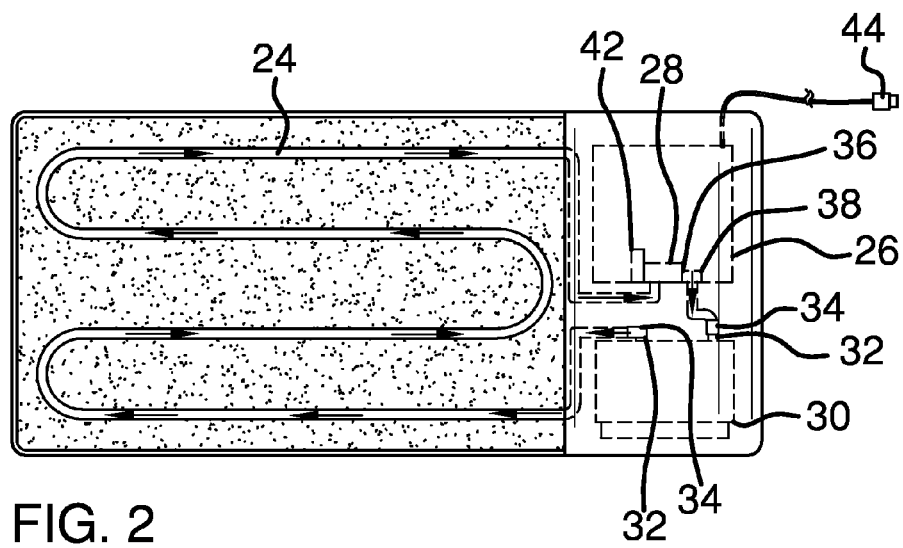
FIG. 2 is a cross-sectional view of an embodiment of the disclosure taken along line 2-2 of FIG. 1.
Figure 3:
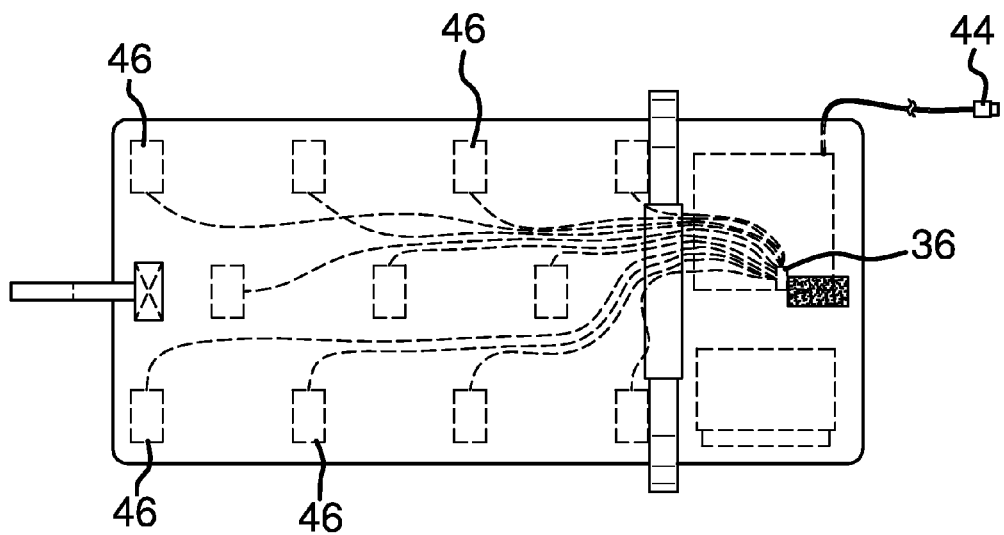
FIG. 3 is a bottom view of an embodiment of the disclosure.
Figure 4:
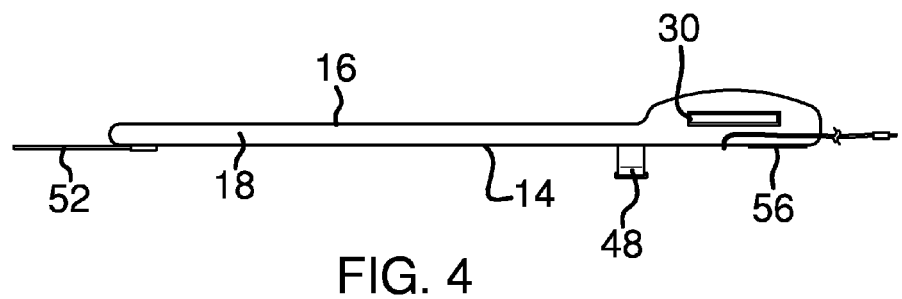
FIG. 4 is a side view of an embodiment of the disclosure.
Figure 5:
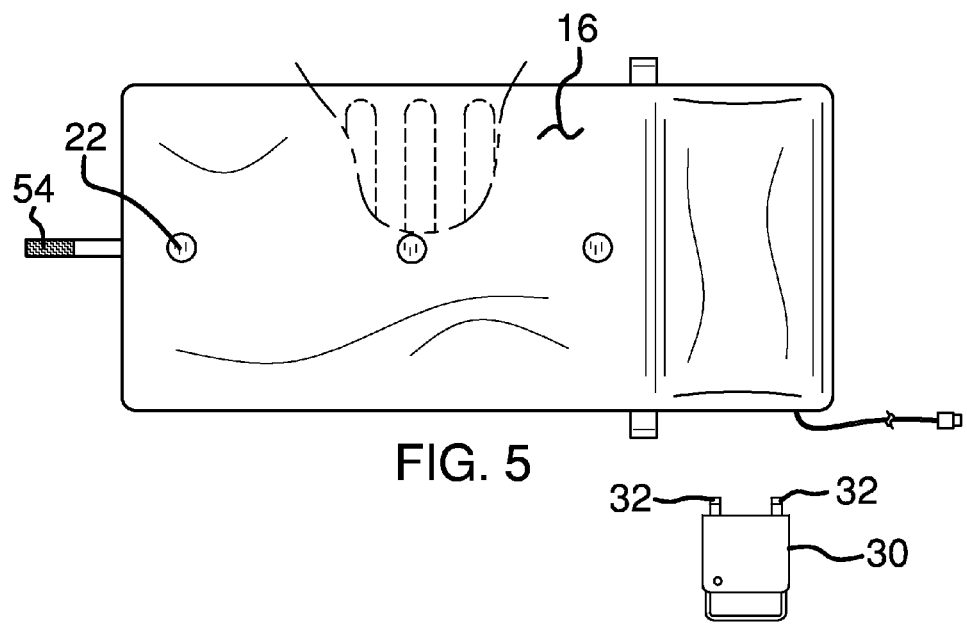
FIG. 5 is a top view of an embodiment of the disclosure.

With reference now to the drawings, and in particular to FIGS. 1 through 8 thereof, a new mat device embodying the principles and concepts of an embodiment of the disclosure and generally designated by the reference numeral 10 will be described.

As best illustrated in FIGS. 1 through 8, the heating and cooling mat assembly 10 generally comprises a mat 12 that has a bottom wall 14, a top wall 16 and a perimeter wall 18 that is attached to and extends between the bottom 14 and top 16 walls. The mat 12 may comprise a housing which may be inflated. Alternatively, the mat 12 may be comprised of a resiliently compressible material and may be generally solid in construction and comprise a foamed elastomeric material. The mat 12 may have a length between 4.0 feet and 7.0 feet and a width between 2.0 feet and 4.0 feet. A raised section 20 may be positioned adjacent to an end of the mat 12 to form a pillow structure. Magnets 22, and in particular neodymium magnets, may be mounted in the mat 12 for pain relief.

A conduit 24 is positioned in the mat 12. The conduit 24 extends through multiple areas of the mat 12 and may, in particular, be placed in a serpentine pattern within the mat 12. The conduit 24 has fluid therein and the conduit 24 may comprise a flexible, plastic or elastomeric construction. The fluid may comprise water. A pump 26 is in fluid communication with the conduit 24 to pump the fluid through the conduit 24 when the pump is 26 turned on. A heat emitter 28 is thermal communication with the liquid in the conduit 24. The heat emitter 28 warms the liquid when the heat emitter 28 is turned on. In this manner the mat 12 is warmed.

A cartridge 30 is removably couplable to the mat 12. The cartridge 30 includes a pair of first ports 32 and the conduit 24 is in fluid communication with a pair of second ports 34. Each of the first ports 32 is removably coupled to one of the second ports 34 to fluidly couple the conduit 24 to the cartridge 30. The cartridge 30 is fillable with a cold fluid. Thus, the conduit 24 is cooled when the pump 26 is turned on after the cartridge 30, with cold fluid therein, is coupled to the conduit 24. The cartridge 30 may be removed as needed to add cold fluid to the cartridge to allow the assembly 10 to be used for heating or cooling the person. The cartridge 30 also be placed in a refrigerator when not in use to cool the contents thereof. The first 32 and second 34 ports are conventional water connection valves which seal when not connected to each other.

A control circuit 36 is electrically coupled to the pump 26 and the heat emitter 28. The control circuit 36 is actuated to turn on the pump 26 and the heat emitter 28. A wireless transmitter 38 is electrically coupled to the control circuit 36. The wireless transmitter 38 is configured to receive wireless signals to actuate the control circuit 36. The wireless transmitter 38 may use Blue Tooth, WiFi or other conventional wireless technologies to allow the wireless transmitter 38 to communicate with a personal computing device 40 such as a smart phone, tablet computer or the like. The personal computing device 40 may then be used to control the pump 26 and heat emitter 28 and in particular to select the temperature the heat emitter 28 will warm the fluid. A battery 42 is mounted in the mat 12 and is electrically coupled to the control circuit 36. The battery 42 may comprise a rechargeable battery and thus a power port 44 may be mounted on the mat and electrically coupled to the battery 42 to recharge the battery 42. The power port 44 may have a dual purpose as a data port as well which may be coupled to the personal computing device 40 for control or programming of the assembly 10.

A plurality of vibrating assemblies 46 is positioned between the top 16 and bottom 14 walls. The vibrating assemblies 46 are spaced from each other and are configured to massage a person lying on the mat 12. The vibrating assemblies 46 are each electrically coupled to the control circuit 36. The personal computing device 40 may be programmed to therefore also control the intensity of the vibrating assemblies 46.

Figure 6:
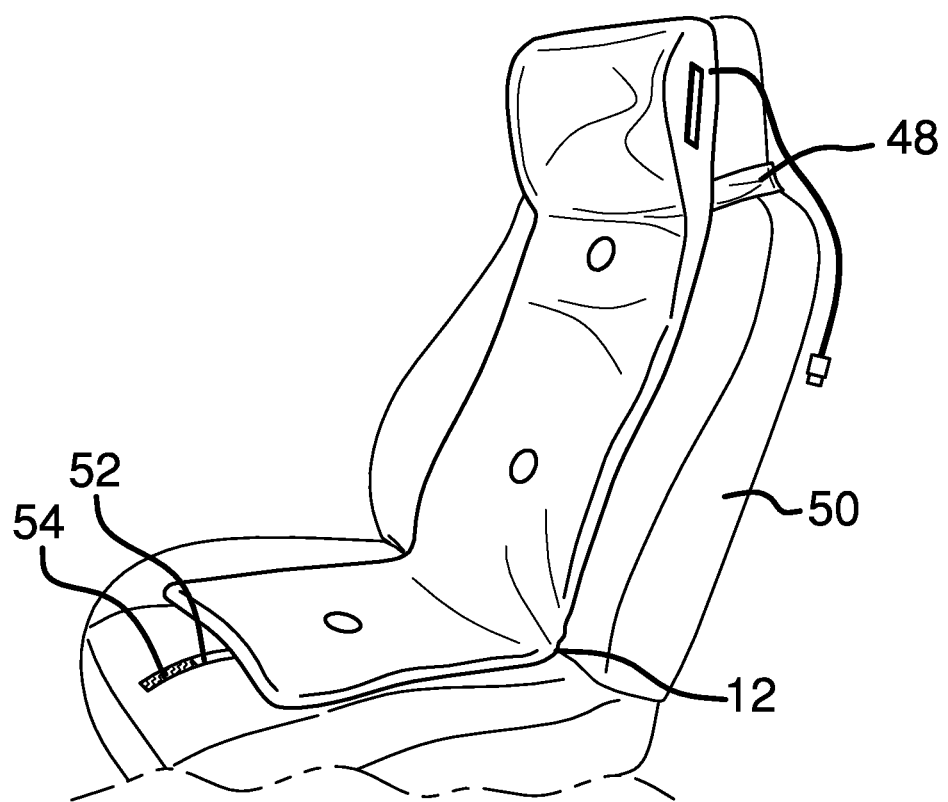
FIG. 6 is a side perspective view of an embodiment of the disclosure.
Figure 7:
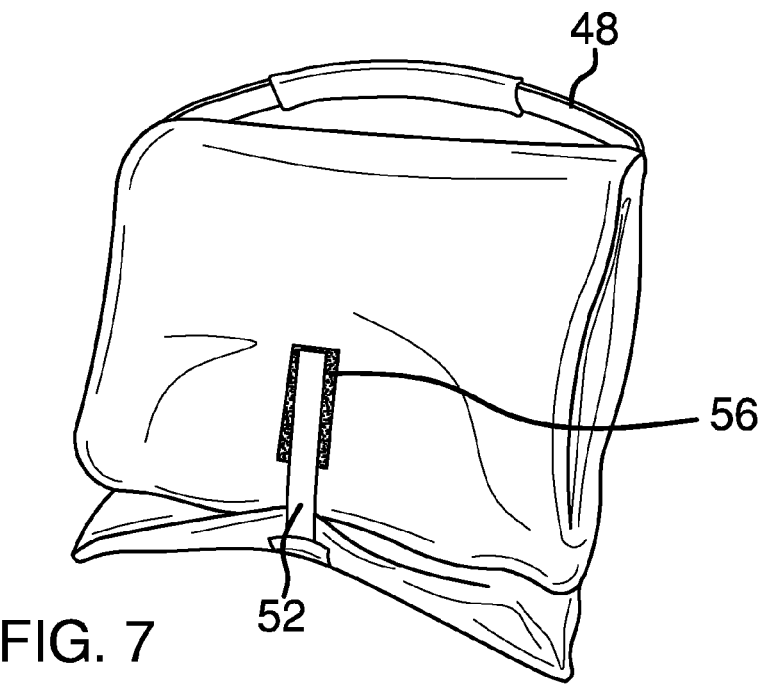
FIG. 7 is a perspective view of an embodiment of the disclosure.
Figure 8:
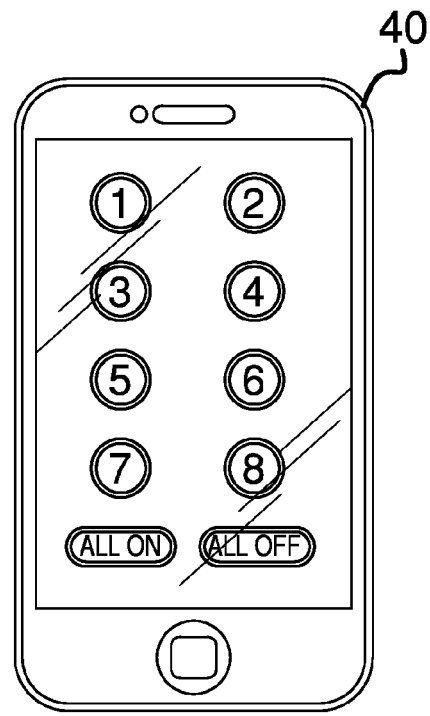
FIG. 8 is a front view of a control of an embodiment of the disclosure.

A mounting strap 48 may be provided for mounting the mat 12 onto a chair 50 as shown in FIG. 6. The mounting strap 48 may be comprised of a resiliently stretchable material and may be positioned adjacent to an end of the mat 12 such as near the raised section 20. The mounting strap 48 traverses the back wall 14 of the mat 12 and may also be utilized for carrying the mat 12.

A securing strap 52 is attached to the back wall 14 adjacent to one end of the mat. A first mating member 54 of a coupler is attached to the securing strap 52. A second mating member 56 is attached to the back wall 14 adjacent to another end of the mat 12. This allows the mat 12 to be folded in half so that the first 54 and second 56 mating members may be joined as in FIG. 7.

In use, the assembly 10 is used in a conventional manner to relax a person by heat, massage or the like. However, the cartridge 30 allows a user to cool the mat 12 if desired. Moreover, the wireless transmitter 38 allows a user of the assembly 10 to easily control the pump 26, heat emitter 28 and vibrating assemblies 46. This may include the amount of time each element is turned on as well as the intensity of the vibrating assemblies 46 and the heat output of the heat emitter 28 to control the temperature of the fluid.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pad assembly comprising:
a mat having a bottom wall, a top wall and a perimeter wall being attached to and extending between said bottom and top walls;
a conduit being positioned in said mat, said conduit being placed in a serpentine pattern within said mat, said conduit having fluid therein;
a pump being in fluid communication with said conduit, said pump pumping the fluid through said conduit when said pump is turned on;
a heat emitter being thermal communication with the liquid in said conduit, said heat emitter warming the liquid when said heat emitter is turned on; and
a cartridge being removably couplable to said mat such that said cartridge is positioned within said mat when coupled to said mat, said cartridge including a pair of first ports, said conduit being in fluid communication with a pair of second ports, each of said first ports being removably coupled to one of said second ports to fluidly couple said conduit to said cartridge, said cartridge being fillable with a cold fluid, wherein said conduit is cooled when said pump is turned on and said cartridge is coupled to said conduit with cold fluid being within said cartridge.

2. The pad assembly according to claim 1, further including a control circuit being electrically coupled to said pump and said heat emitter, said control circuit being actuated to turn on said pump and said heat emitter.

3. The pad assembly according to claim 2, further including a wireless transmitter being electrically coupled to said control circuit, said wireless transmitter being configured to receive wireless signals to actuate said control circuit.

4. The pad assembly according to claim 2, further including a battery being mounted in said mat and being electrically coupled to said control circuit.

5. The pad assembly according to claim 4, wherein said battery comprises a rechargeable battery.

6. The pad assembly according to claim 2, further including a plurality of vibrating assemblies being positioned between said top and bottom walls, said vibrating assemblies being spaced from each other and being configured to massage a person lying on said mat, said vibrating assemblies each being electrically coupled to said control circuit.

7. The pad assembly according to claim 1, further including a plurality of vibrating assemblies being positioned between said top and bottom walls, said vibrating assemblies being spaced from each other and being configured to massage a person lying on said mat.

8. A pad assembly comprising:
a mat having a bottom wall, a top wall and a perimeter wall being attached to and extending between said bottom and top walls, said mat being comprised of a resiliently compressible material;
a conduit being positioned in said mat, said conduit being placed in a serpentine pattern within said mat, said conduit having fluid therein;
a pump being in fluid communication with said conduit, said pump pumping the fluid through said conduit when said pump is turned on;
a heat emitter being thermal communication with the liquid in said conduit, said heat emitter warming the liquid when said heat emitter is turned on;
a cartridge being removably couplable to said mat such that said cartridge is positioned within said mat when coupled to said mat, said cartridge including a pair of first ports, said conduit being in fluid communication with a pair of second ports, each of said first ports being removably coupled to one of said second ports to fluidly couple said conduit to said cartridge, said cartridge being fillable with a cold fluid, wherein said conduit is cooled when said pump is turned on and said cartridge is coupled to said conduit with cold fluid being within said cartridge;
a control circuit being electrically coupled to said pump and said heat emitter, said control circuit being actuated to turn on said pump and said heat emitter;
a wireless transmitter being electrically coupled to said control circuit, said wireless transmitter being configured to receive wireless signals to actuate said control circuit;

a battery being mounted in said mat and being electrically coupled to said control circuit, said battery comprising a rechargeable battery; and a plurality of vibrating assemblies being positioned between said top and bottom walls, said vibrating assemblies being spaced from each other and being configured to massage a person lying on said mat, said vibrating assemblies each being electrically coupled to said control circuit.

\* \* \* \* \*